US00PP33517P2

(12) United States Plant Patent
Farrow

(10) Patent No.: US PP33,517 P2
(45) Date of Patent: Sep. 28, 2021

(54) ***LAGERSTROEMIA* PLANT NAMED 'STRAWCONBEL'**

(50) Latin Name: *Lagerstroemia indica*
Varietal Denomination: Strawconbel

(71) Applicant: THE CONARD PYLE COMPANY, West Grove, PA (US)

(72) Inventor: Michael W. Farrow, Warwick, MD (US)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 17/137,687

(22) Filed: Dec. 30, 2020

(51) Int. Cl.
*A01H 5/00* (2018.01)

(52) U.S. Cl.
USPC ..... Plt./252

(58) Field of Classification Search
USPC ..... Plt./252
See application file for complete search history.

(56) References Cited

U.S. PATENT DOCUMENTS

PP28,281 P2 8/2017 Hansen

OTHER PUBLICATIONS

"Shrubs Vines Trees Evergreens Edibles" 2021 Star® Roses and Plants Catalog, published on Feb. 23, 2020, pp. 11, 62, and 88.

*Primary Examiner* — Annette H Para
(74) *Attorney, Agent, or Firm* — Panitch Schwarze Belisario & Nadel LLP; Stephany G. Small; Travis W. Bliss

(57) ABSTRACT

A new and distinct variety of *Lagerstroemia* plant, referred to by its cultivar name, 'Strawconbel', is disclosed. The new variety forms attractive red colored flowers. Attractive, medium green colored foliage is formed. The growth habit is compact and low-mounded. The new variety is well suited for providing attractive ornamentation in the landscape.

2 Drawing Sheets

Figure 1:
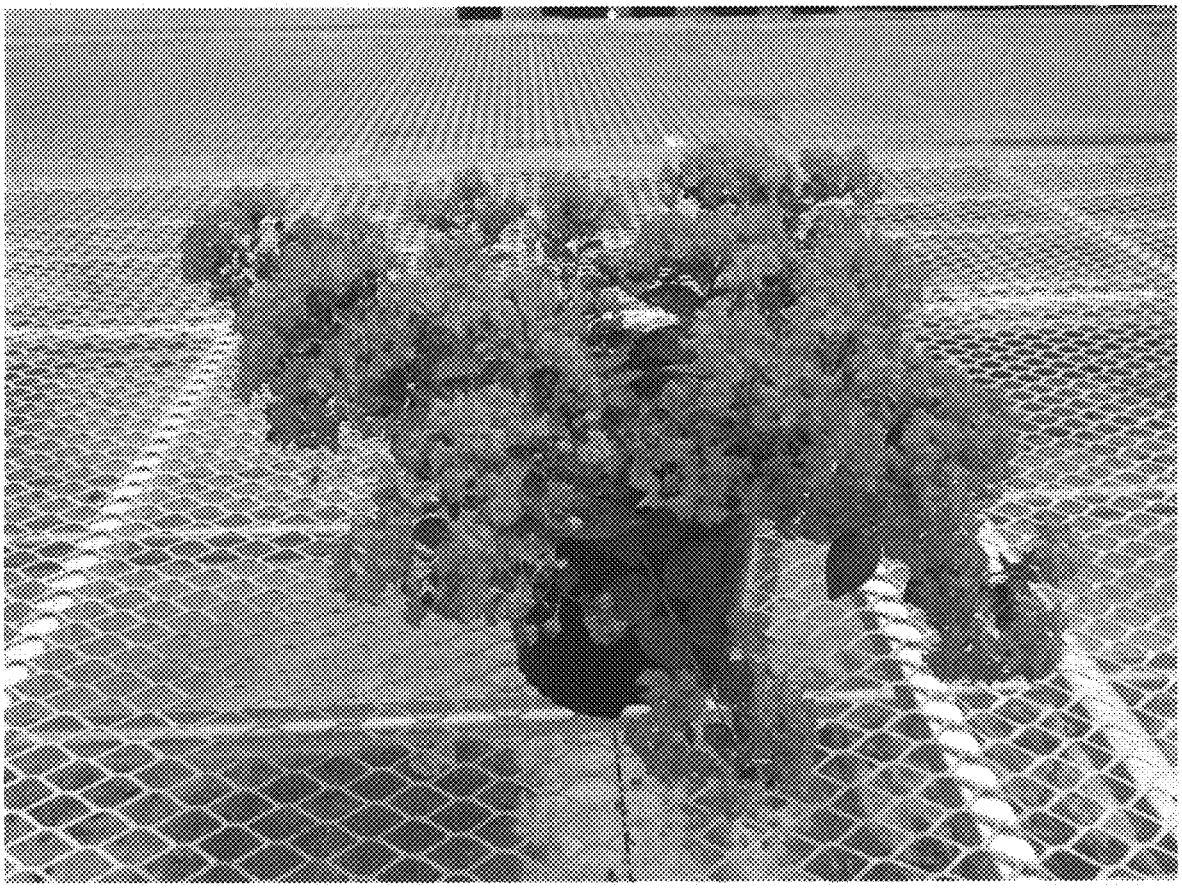

Botanical/commercial classification:
Latin name: *Lagerstroemia indica.*
Varietal denomination: 'Strawconbel'.

SUMMARY OF THE INVENTION

The new variety of *Lagerstroemia indica* plant originated in a controlled breeding program in Earleville, Md. during 2016. The objective of the breeding program was the development of a series of *Lagerstroemia* cultivars having abundant inflorescences with attractive flower coloration, compact growth habits, and good disease resistance. The new cultivar was created by open pollination. The female parent (i.e., the seed parent) was the 'Twilight' variety (non-patented). The male parent (i.e., the pollen parent) was unknown.

The parentage of the new variety can be summarized as follows:

'Twilight' x unknown variety

The new cultivar was discovered and selected as a single flowering plant from the progeny resulting from the above open pollination during August 2017 in a controlled environment in Earleville, Md. Selective study resulted in the identification of a single plant of the new variety.

It was found that the new variety of *Lagerstroemia* plant of the present invention:

(a) forms red colored flowers,
(b) displays medium green colored foliage, and
(c) exhibits a moderately vigorous, compact, and low-mounded growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'Twilight' variety (i.e., the seed parent) displays purple colored flowers and an upright growth habit, whereas the new variety provides red colored flowers and a compact and low-mounded growth habit. Moreover, the new variety can also be distinguished from other similar varieties that are commercially available. For instance, the new variety of the present invention can readily be distinguished from the 'Cherry Mocha' variety (U.S. Plant Pat. No. 28,281), as the new cultivar produces more flowers per plant and a more compact growth habit compared to the 'Cherry Mocha' variety and the new cultivar displays green colored foliage, whereas the 'Cherry Mocha' variety displays burgundy colored foliage.

The new variety has been found to undergo asexual propagation by terminal stem cuttings. Asexual propagation by terminal stem cuttings in Cochranville, Pa. since August 2017 has shown that the characteristics of the new variety are stable and are strictly transmissible by such asexual propagation from one generation to another. Accordingly, the new variety undergoes asexual propagation in a true-to-type manner.

The new variety has been named 'Strawconbel'.

The new variety was first offered for sale on Jan. 8, 2020 at Baltimore, Md. by the inventor or by another who obtained the new variety directly or indirectly from the inventor. The new variety was also offered for sale in the "SHRUBS VINES TREES EVERGREENS EDIBLES" 2021 Star® *Roses and Plants Catalog*, which was published on Feb. 23, 2020 by the inventor or by another who obtained the new variety directly or indirectly from the inventor.

BRIEF DESCRIPTION OF THE PHOTOGRAPHS

The accompanying photographs show as nearly true as it is reasonably possible to make the same, in a color illustration of this character, typical specimens of the plant and plant parts of the new variety. Colors in the photographs may differ slightly from the color values cited in the detailed description, which accurately describes the colors of the 'Strawconbel' variety. The plants were finished plants flowering in June 2019 and grown inside in one-gallon containers for at Cochranville, Pa.

FIG. 1—illustrates a specimen of the plant displaying the overall growth and flowering habit—side view.

Figure 2:
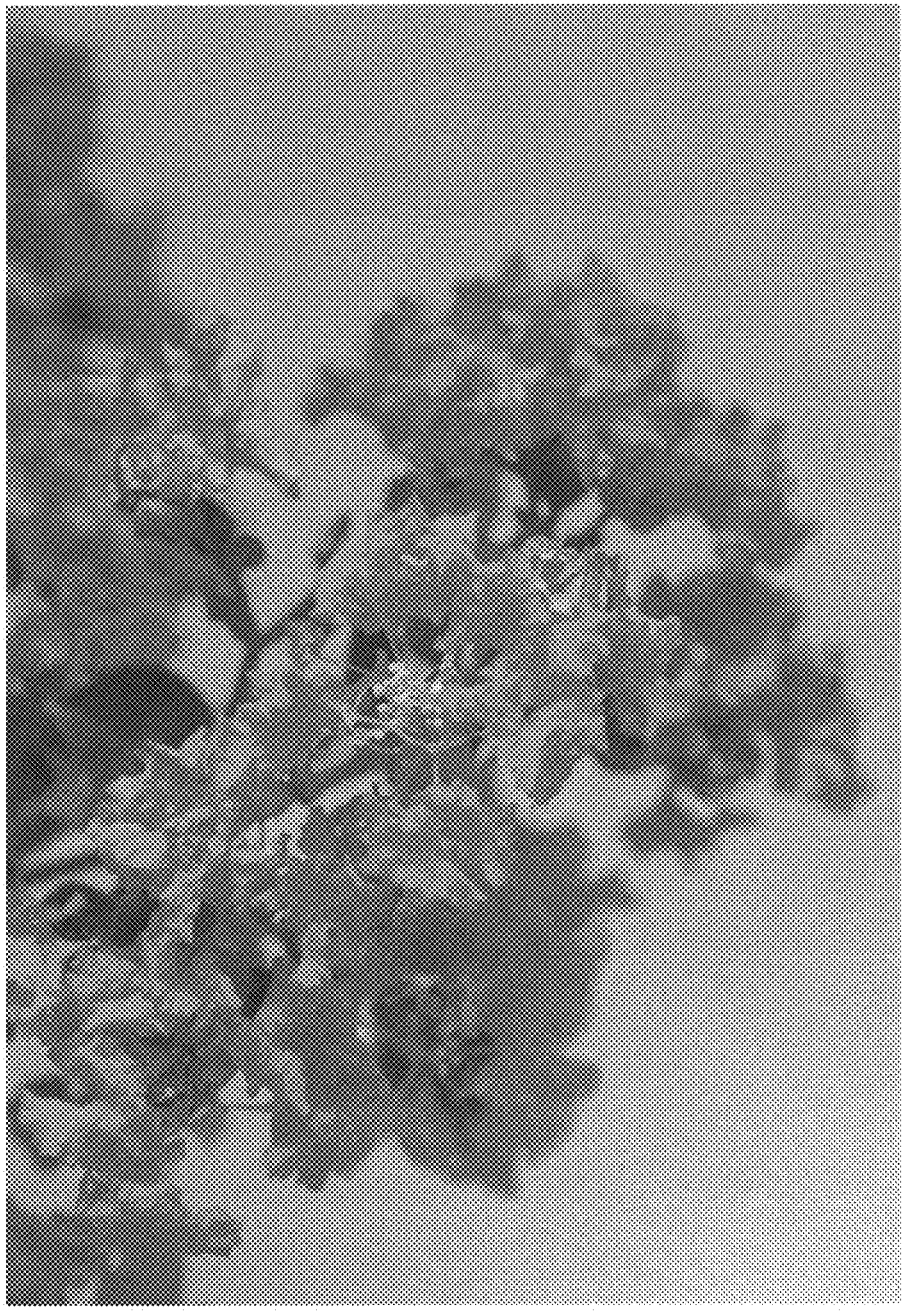

FIG. 2—illustrates a specimen of an individual inflorescence.

DETAILED BOTANICAL DESCRIPTION

The chart used in the identification of the colors is that of The Royal Horticultural Society (R.H.S. Color Chart), 2015 edition, London, England. The terminology which precedes reference to the chart has been added to indicate the corresponding color in more common terms. The color values were determined in April 2021 under natural light conditions in Cochranville, Pa.

The following descriptions and measurements describe approximately one-year plants produced from cuttings from stock plants and grown under conditions comparable to those used in commercial nursery production. Plants were grown outdoors under standard nursery practices during the 2020 growing season and then moved into a greenhouse in January 2021 and grown for four months in Cochranville, Pa. Measurements and numerical values represent averages of tygical plants.

Parentage:

*Female parent*.—'Twilight' (non-patented).

*Male parent*.—Unknown.

Propagation:

*Type cutting*.—Terminal cuttings.

*Time to initiate roots*.—Approximately 16 days.

*Time to produce*.

*A rooted cutting*.—Approximately 39 days.

*Root description*.—Fibrous and fine; white to brown in color.

*Rooting habit*.—Freely branching; dense.

Plant:

*Growth habit and general appearance*.—Multi-stemmed deciduous shrub, moderately vigorous and compact, low, mounding growth habit.

*Size*.—Height from soil level to top of plant plane: approximately 34.0 cm.

—Width: approximately 43.0 cm.

*Branching habit*.—Freely branching; pinching enhances branching.

—Quantity of lateral branches per plant: approximately 5 main stems per plant with approximately 5 lateral branches per stem.

*Trunk*—Diameter at soil level: approximately 6.0 mm.

—Diameter at midpoint: approximately 3.0 mm.

—texture: woody, slight exfoliation with age.

—color: commonly near Brown Group 200A.

*Branch*.—Shape: quadrangulate with rounded wings.

—Strength: strong.

—Arrangement: subopposite to alternate.

—Aspect: erect to 45° angle from main stem.

—Length to base of inflorescence: approximately 17.0 cm to 22.0 cm.

—Diameter: approximately 3.0 mm.

—Length of central internode: approximately 2.5 cm.

—Texture of young stem: glabrous.

—Texture of mature stem: woody, rough.

—Color of young stem: commonly near Red-Purple Group 60C.

—Color of mature stem: commonly near Brown Group 200A.

Foliage:

*General sescription*.—Form: simple.

—Arrangement: subopposite to alternate.

—Fragrance: none detected.

*Leaves*.—Shape: ovate to elliptic.

—Margin: entire.

—Apex: cuspidate.

—Base: attenuate.

—Venation pattern: pinnate.

—Length of mature leaf: approximately 4.0 cm.

—Width of mature leaf: approximately 2.5 cm.

—Texture of upper and lower surfaces: glabrous.

—Color of upper surface of young foliage: commonly near Green Group 137C with venation color of commonly near Green Group 137D.

—Color of lower surface of young foliage: commonly near Green Group 138B with venation color of commonly near Green Group 138C.

—Color of upper surface of mature foliage: commonly near Green Group 137A with venation color of commonly near Green Group 137B.

—Color of lower surface of mature foliage: commonly near Green Group 138B with venation color of commonly near Green Group 138D.

*Petiole*.—Length: approximately 2.0 mm.

—Diameter: approximately 3.0 mm.

—Texture: Glabrous.

—Color: commonly near Greyed-Orange Group 176B.

Flowering Description:

*Flowering season*.—Flowers in mid-summer through early fall.

*Lastingness of individual inflorescence on the plant*.—Approximately 1 to 2 weeks.

*General description*.—Type:panicle, flowers self-cleaning.

—Quantity per plant: approximately 20.

—Fragrance: faint sweet.

—Aspect: upward to outward.

—Height: approximately 7.0 cm.

—Width: approximately 8.0 cm.

—Quantity of flowers per inflorescence: approximately 20.

*Peduncle*.—Strength: strong.

—Shape: rounded.

—Aspect: erect to about 45° from branch axis.

—Length: approximately 1.0 cm.

—Diameter: approximately 2.0 mm.

—Texture: glabrous.

—Color: commonly near Red-Purple Group 59C.

Flower:

*Bud just before opening*.—Shape: globose.
—Length: approximately 6.0 mm.
—Diameter: approximately 6.0 mm.
—Color: commonly near Red-Purple Group 59D.
*Corolla*.—Shape: rotate.
—Depth: approximately 1.0 cm.
—Diameter: approximately 3.0 cm.
*Petals*.—Shape: ovate.
—Margin: crisped, undulating.
—Apex: acute.
—Base: truncate.
—Length: approximately 1.5 cm.
—Width: approximately 1.1 cm.
—Texture of upper and lower surfaces: glabrous.
—Color of upper and lower surfaces: commonly near Purple-Violet Group N80A.
*Calyx*.—Shape: round.
—Depth: approximately 6.0 mm.
—Diameter: approximately 6.0 mm.
*Sepals*.—Shape: triangular.
—Margin: smooth, entire.
—Apex: acute.
—Base: truncate.
—Length: approximately 3.0 mm.
—Width: approximately 3.0 mm.
—Texture of upper surface: glabrous.
—Texture of lower surface: glabrous.
—Color of upper surface: commonly near Red-Purple Group 59C.
—Color of lower surface: commonly near Yellow-Green Group 149D.
*Pedicel*.—Strength: strong.
—Aspect: erect, to about 45° from peduncle.
—Length: approximately 6.0 mm.
—Diameter: approximately 1.5 mm.
—Texture: glabrous.
—Color: commonly near Red-Purple Group 59C.
*Reproductive organs*.—Androecium:
Stamen quantity per flower: approximately 30 to 36.
Stamen length: approximately 9.5 mm.
Filament color: commonly near Red-Purple Group 62A.
Anther shape: narrow oblong, dorsifixed.
Anther length: approximately 8.0 mm.
Anther color: commonly near Yellow-Orange Group 14B.
Pollen amount: abundant.
Pollen color: commonly near Yellow-Orange Group 14B.
Gynoecium:
Pistil quantity per flower: 1.
Pistil length: approximately 1.6 cm.
Stigma shape: rounded.
Stigma color: commonly near Green Group 133A.
Style length: approximately 1.3 cm.
Style color: commonly near Red-Purple Group 59C.
Ovary length: approximately 3.0 mm.
Ovary color: commonly near Yellow Group 3A.
—Seed and fruit production: neither seed nor fruit production has been observed to date.

Development:

*Disease and pest resistance*.—Resistance to pathogens and pests common to Langerstroemia has not been observed to date.
*Commercial crop time*.—Approximately 15 weeks from a rooted cutting to finish in a 19.0 cm pot.
*Hardiness*.—USDA Zone 6*b* (−5° F.).
*Heat tolerance*.—Regularly tolerates temperatures as high as 38.3° C. (101° F.) in the summer.

The new 'Strawconbel' variety has not been observed under all possible environmental conditions to date. Accordingly, it is possible that the phenotypic expression may vary somewhat with changes in light intensity and duration, cultural practices, and other environmental conditions, without, however, any variance in genotype.

I claim:

1. A new and distinct cultivar of *Lagerstroemia* plant characterized by the following combination of characteristics:

(a) forms red colored flowers,
(b) displays medium green colored foliage, and
(c) exhibits a moderately vigorous, compact, low-mounded growth habit;

substantially as herein shown and described.

* * * * *